(12) United States Patent
Lau

(10) Patent No.: US 6,673,591 B2
(45) Date of Patent: *Jan. 6, 2004

(54) METHODS FOR ENHANCING THE PRODUCTION OF VIRAL VACCINES IN CELL CULTURE

(75) Inventor: Allan S. Lau, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 161 days.

This patent is subject to a terminal disclaimer.

(21) Appl. No.: 09/736,748

(22) Filed: Dec. 13, 2000

(65) Prior Publication Data

US 2001/0001290 A1 May 17, 2001

Related U.S. Application Data

(63) Continuation of application No. 09/137,661, filed on Aug. 20, 1998, now abandoned, which is a continuation of application No. 08/700,198, filed on Aug. 21, 1996, now Pat. No. 5,840,565.
(60) Provisional application No. 60/002,621, filed on Aug. 22, 1995.

(51) Int. Cl.$^7$ ............................. C12N 7/01; C12N 7/02; C12N 15/00; C12N 5/00; C07H 21/04; C07H 21/02; C07H 21/00; A61K 39/12
(52) U.S. Cl. ................... 435/235.1; 435/239; 435/69.3; 435/325; 536/23.2; 536/24.5; 536/25.2; 536/25.3; 424/204.1
(58) Field of Search ............................. 435/183, 235.1, 435/325, 69.2, 69.3, 239.4, 239; 424/206.1, 204.1; 536/23.2, 24.5, 25.2, 25.3, 24.1

(56) References Cited

U.S. PATENT DOCUMENTS

| | | | |
|---|---|---|---|
| 4,579,821 A | 4/1986 | Palmiter et al. | 435/91.41 |
| RE33,164 E | 2/1990 | Brown | |
| 5,149,531 A | 9/1992 | Younger | 424/93.6 |
| 5,525,513 A | 6/1996 | Chen | 435/320.1 |
| 5,840,565 A | * 11/1998 | Lau | 435/235.1 |

FOREIGN PATENT DOCUMENTS

| | | |
|---|---|---|
| EP | 0 414 475 A1 | 2/1991 |
| WO | WO 93 20188 A | 10/1993 |

OTHER PUBLICATIONS

Fields et al. Fields Virology, third edition, vol. 1. Philadelphia: Lippencott Williams and Wilkins, pp. 386–389.*
Meurs et al. Journal of Virology. 1992; 66 (10): 5805–5814.*
Aguzzi et al., *Brain Pathology* (1994) 4:3–20.
Barber et al., *Proc. Natl. Acad. Sci. USA*, (1994) 91:4278–4282.
Busby et. al., *J. Mol. Biol.* (1982) 154:197–209.

Camper et al., *Biology of Reproduction* (1995) 52:246–257.
Candal et al., *Biologicals* (1991) 19:213–218.
Chong et al., *EMBO J.* (1992) 11:1553–1562.
D'Addario et al., *J. Virol.* (1990) 64:6080–6089.
Deng et al., *Analytical Biochemistry* (1992) 200:81–88.
Du et al., *Cell* (1993) 74:887–898.
Feng et al., *Proc Natl Acad Sci USA* (1992) 89:5447–5451.
Galabru et al., *J. Biol. Chem.* (1987) 262:15538–15544.
Green SR et al., *Genes & Development* (1992) 6:2478–2490.
Gutterman, *Natl. Acad. Sci.* (1994) 91:1198–1205.
Hassel et al., *Methods* (1994) 50:323–334.
Henry et al., *J. Biol. Regulators and Homeostatic Agents* (1994) 8:1:15–24.
Hershey et al., *Ann. Rev. Biochem.* (1991) 60:717–755.
Jaramillo et al., *Cancer Investigation* (1995) 13:327–337.
Koromilas et al., *Science* (1992) 257:1685–1689.
Kumar et al., *Natl. Acad. Sci. USA* (1994) 91:6288–6292.
Lee et al., *Virol.* (1993) 193:1037–1041.
Lee et al., *Virology* (1993) 192:380–385.
MacDonald et al., *Critical Reviews Biotech.* (1990) 10:155–178.
Maran et al., *Science* (1994) 265:789–792.
Marcus et al., *J. Gen. Virol.* (1988) 69:1637–1645.
Matsuyama et al., *Cell* (1993) 75:83–97.
McCormack et al., *Virology* (1994) 198:92–99.
McMillan et al., *J. Biol. Chem.* (1995) 270:2601–2606.
Meurs et al., *Cell* (1990) 62:379–390.
Meurs et al., *Proc. Natl. Acad. Sci. USA* (1993) 90:232–236.
Meurs et al., *J. Virol.* (1992) 66:5805–5814.
Ozes et al., *J. Interferon Res.* (1994) 14:25–32.
Pearson, *Devel. Biol. Standard.* (1992) 76:13–17.
Peetermans, *J. Vaccine* (1992) 10 supp 1:S99–S101.
Pestka et al., *Ann. Rev. Biochem.* (1987) 56:727–777.
Proud C.G., *Trends Biochem. Sci. (TIBS)*, (1995) 20:6:241–246.
Read et al., *J. Infect. Dis.* (1985) 152:466–472.
Robertson et al., *J. Gen. Virol.* (1991) 72:2671–2677.
Sen et al., *J. Biol. Chem.* (1992) 267:5017–5020.
Shevitz et al., in *Viral Vaccines* Mizrahi, A. ed pp1–35 (1990) Wiley–Liss.

(List continued on next page.)

*Primary Examiner*—James Housel
*Assistant Examiner*—Shanon Foley
(74) *Attorney, Agent, or Firm*—Carol L. Francis; Bozicevic, Field & Francis LLP

(57) ABSTRACT

Methods for enhancing the production of viral vaccines in animal cell culture are described. These methods rely on the manipulation of the cellular levels of certain interferon induced antiviral activities, in particular, cellular levels of double-stranded RNA (dsRNA) dependent kinase (PKR) and 2'-5' oligoadenylate synthetase (2-5A synthetase). In cell cultures deficient for PKR or 2-5A synthetase, viral yield is enhanced by several orders of magnitude over cell cultures with normal levels of these proteins making these cell cultures useful for the production of viral vaccines.

13 Claims, 2 Drawing Sheets

OTHER PUBLICATIONS

Tanaka et al., *Adv. Immunol.* (1992) 52:263–281.
Tannock et al., *Vaccine* (1985) 3:333–339.
Taylor et al., *Virus Research* (1990) 15:1–26.
Thomas et al., *J. Immunol* (1993) 150:12:5529–5534.
Visvanathan et al., *EMBO J.* (1989) 8:1129–1138.
Williams, *Eur. J. Biochem.* (1991) 200:1–11.
Wood et al., *Biologicals* (1990) 18:143–146.
Zinn et al., *Science* (1988) 240:210–213.
Hovanessian, Ara G., "The double stranded RNA–activated protein kinase induced by interferon:dsRNA–PK," J. Interferon Res., vol. 9(6):641–7 (1989).
Samuel, Charles E.; Ozato, Keiko, "induction of interferons and interferon–induced genes," Biotherapy (Dordrecht, Neth.), vol. Date 1994, 8(3/4, Cytokine Yearbook, vol. 1), 183–187.

Bowie et al., "Deciphering the Message in Protein Sequences: Tolerance to Amino Acid Substitutions," Science, vol. 247:1306–1310 (1990).

Der, S.D., et al., Involvement of the double–stranded RNA–dependent kinase PKR in interferon expression and interferon–mediated antiviral activity, Proc. Natl. Acad. Sci. USA, vol. 92:8841–8845 (1995).

Clemens, Michael J., *Int, J. Biochem Cell Biol.* (1997) 29:7:945–949.

Zurcher et al., Journal of Virology, 66:8:5059–5066 (1992).

* cited by examiner

METHODS FOR ENHANCING THE PRODUCTION OF VIRAL VACCINES IN CELL CULTURE

CROSS REFERENCE TO RELATED APPLICATIONS

This application is a continuation of U.S. Ser. No. 09/137,661 filed Aug. 20, 1998 now abandoned, which in turn is a continuation of U.S. Ser. No. 08/700,198 filed Aug. 21, 1996 now U.S. Pat. No. 5,840,565, which claims benefit of Provisional Application U.S. Ser. No. 60/002,621 filed Aug. 22, 1995. Each of these cited Applications are hereby incorporated, in their entirety, by reference.

INTRODUCTION

1. Technical Field

The present invention relates to methods for the production of virus for vaccine production in cell culture.

2. Background

Effective control of influenza pandemics depends on early vaccination with the inactivated virus produced from newly identified influenza strains. However, for more effective pandemic control, improvements in the manufacturing and testing of the vaccine are needed. Influenza viruses undergo very frequent mutations of the surface antigens. Consequently, vaccine manufacturers cannot stock-pile millions of doses for epidemic use. Current influenza control methods demand constant international surveillance and identification of any newly emergent strains coupled with vaccine production specific for the newly identified strains. Current influenza vaccine production, which requires the use of embryonated eggs for virus inoculation and incubation, is cumbersome and expensive. It can also be limited by seasonal fluctuations in the supply of suitable quality eggs. Thus, for production of mass doses of monovalent vaccine in a short time, it would be advantageous to develop alternate, egg-independent production technology. In this respect, production of an influenza vaccine on a stable cell line may solve many of the problems in mass production. However, the yield of human influenza viruses on tissue culture is disappointingly much lower than in embryonated eggs (Tannock et al. Vaccine 1985 3:333–339). To overcome these limitations and improve the quality of vaccines, it would be advantageous to develop cell culture lines which provide an enhanced yield of virus over those currently available.

In using mammalian cell lines for whole virion vaccine production, a common problem for vaccine manufacturers is that mammalian cells have intrinsic antiviral properties, specifically, the interferon (IFN) system, which interferes with viral replication. IFNs can be classified into two major groups based on their primary sequence. Type I interferons, IFN-α and IFN-β, are encoded by a super family of intronless genes consisting of the IFN-α gene family and a single IFN-β gene. Type II interferon, or IFN-γ, consists of only a single type and is restricted to lymphocytes (T-cells and natural killer cells). Type I interferons mediate diverse biological processes including induction of antiviral activities, regulation of cellular growth and differentiation, and modulation of immune functions (Sen, G. C. & Lengyel, P. (1992) J. Biol. Chem. 267, 5017–5020; Pestka, S. & Langer, J. A. (1987) Ann. Rev. Biochem. 56, 727–777). The induced expression of Type I IFNs, which include the IFN-α and IFN-β gene families, is detected typically following viral infections. Many studies have identified promoter elements and transcription factors involved in regulating the expression of Type I IFNs (Du, W., Thanos, D. & Maniatis, T. (1993) Cell 74, 887–898; Matsuyama, T., Kimura, T., Kitagawa, M., Pfeffer, K., Kawakami, T., Watanabe, N., Kundig, T. M., Amakawa, R., Kishihara, K., Wakeham, A., Potter, J., Furlonger, C. L., Narendran, A., Suzuki, H., Ohashi, P. S., Paige, C. J., Taniguchi, T. & Mak, T. W. (1993) Cell 75, 83–97; Tanaka, N. & Taniguchi, T. (1992) Adv. Immunol. 52, 263–81). However, it remains unclear what are the particular biochemical cues that signify viral infections to the cell and the signaling mechanisms involved (for a recent review of the interferon system see Jaramillo et al. Cancer Investigation 1995 13:327–337).

IFNs belong to a class of negative growth factors having the ability to inhibit growth of a wide variety of cells with both normal and transformed phenotypes. IFN therapy has been shown to be beneficial in the treatment of human malignancies such as Kaposi's sarcoma, chronic myelogenous leukemia, non-Hodgkin's lymphoma and hairy cell leukemia as well as the treatment of infectious diseases such as papilloma virus (genital warts) and hepatitis B and C (reviewed by Gutterman Proc. Natl Acad Sci. 91:1198–1205 1994). Recently, genetically-engineered bacterially-produced IFN-β was approved for treatment of multiple sclerosis, a relatively common neurological disease affecting at least 250,000 patients in the US alone.

IFNs elicit their biological activities by binding to their cognate receptors followed by signal transduction leading to induction of IFN-stimulated genes (ISG). Several of them have been characterized and their biological activities examined. The best studied examples of ISGs include a double-stranded RNA (dsRNA) dependent kinase (PKR, formerly known as p68 kinase), 2'-5'-linked oligoadenylate (2-5A) synthetase, and Mx proteins (Taylor J L, Grossberg S E. Virus Research 1990 15:1–26.; Williams B R G. Eur. J. Biochem. 1991 200:1–11). Human Mx A protein is a 76 kD protein that inhibits multiplication of influenza virus and vesicular stomatitis virus (Pavlovic et al. (1990) J. Viol. 64, 3370–3375).

2'-5' Oligoadenylate synthetase (2-5A synthetase) uses ATP to synthesize short oligomers of up to 12 adenylate residues linked by 2'-5'-phosphodiester bonds. The resulting oligoadenylate molecules allosterically activate a latent ribonuclease, RNase L, that degrades viral and cellular RNAs. The 2-5A synthetase pathway appears to be important for the reduced synthesis of viral proteins in cell-free protein-synthesizing systems isolated from IFN-treated cells and presumably for resistance to viral infection in vivo at least for some classes of virus.

PKR (short for protein kinase RNA-dependent) is the only identified double-stranded RNA (dsRNA)-binding protein known to possess a kinase activity. PKR is a serine/threonine kinase whose enzymatic activation requires binding to dsRNA or to single-stranded RNA presenting internal dsRNA structures, and consequent autophosphorylation (Galabru, J. & Hovanessian, A. (1987) J. Biol. Chem. 262, 15538–15544; Meurs, E., Chong, K., Galabru, J., Thomas, N. S., Kerr, I. M., Williams, B. R. G. & Hovanessian, A. G. (1990) Cell 62, 379–390). PKR has also been referred to in the literature as dsRNA-activated protein kinase, P1/eIF2 kinase, DAI or dsI for dsRNA-activated inhibitor, and p68 (human) or p65 (murine) kinase. Analogous enzymes have been described in rabbit reticulocytes, different murine tissues, and human peripheral blood mononuclear cells (Farrel et al. (1977) Cell 11, 187–200; Levin et al. (1978) Proc. Natl Acad. Sci. USA 75, 1121–1125; Hovanessian (1980) Biochimie 62, 775–778; Krust et al. (1982) Virology 120, 240–246; Buffet-Janvresse et al. (1986) J. Interferon Res. 6, 85–96). The best characterized in vivo substrate of PKR is the alpha subunit of eukaryotic initiation factor-2 (e1F-2α) which, once phosphorylated, leads ultimately to inhibition of cellular and viral protein synthesis (Hershey, J. W. B. (1991) *Ann. Rev. Biochem.* 60, 717–755). PKR can phosphorylate initiation factor e1F-2α in vitro when activated by double-stranded RNA (Chong et al. (1992) *EMBO J.* 11, 1553–1562). This particular function of PKR has been suggested as one of the mechanisms responsible for mediating the antiviral and antiproliferative activities of IFN-α and IFN-β. An additional biological function for PKR is its putative role as a signal transducer. Kumar et al. demonstrated that PKR can phosphorylate IκBα, resulting in the release and activation of nuclear factor κB (NF-κB) (Kumar, A., Haque, J., Lacoste, J., Hiscott, J. & Williams, B. R. G. (1994) *Proc. Natl. Acad. Sci. USA* 91, 6288–6292). Given the well-characterized NF-κB site in the IFN-β promoter, this may represent a mechanism through which PKR mediates dsRNA activation of IFN-β transcription (Visvanathan, K. V. & Goodbourne, S. (1989) *EMBO J.* 8, 1129–1138).

The catalytic kinase subdomain of PKR (i.e., of p68 (human) kinase and p65 (murine) kinase) has strong sequence identity (38%) with the yeast GCN2 kinase (Chong et al. (1992) *EMBO J.* 11, 1553–1562; Feng et al. (1992) *Proc. Natl. Acad. Sci. USA* 89, 5447–5451). Recombinant p68 kinase expressed in yeast *Saccharomyces cerevisiae* exhibits a growth-suppressive phenotype. This is thought to be attributed to the activation of the p68 kinase and subsequent phosphorylation of the yeast equivalent of mammalian e1F2α (Chong et al.; Cigan et al. (1982) *Proc. Natl. Acad. Sci. USA* 86, 2784–2788).

The present inventor has surprisingly discovered by manipulating the expression of certain ISGs that manipulation of ISGs can have beneficial uses. They have discovered that suppression of the expression of the PKR protein or the 2-5A synthetase protein or both results in a substantially higher viral yield from virus-infected cells which is useful for enhancing the production of vaccines in animal cell culture.

Relevant Literature

A common approach to examine the biological role of PKR involves the generation of mutants deficient in the kinase activities. Since PKR possesses a regulatory site for dsRNA binding and a catalytic site for kinase activity, investigators have used block deletion or site-directed mutagenesis to generate mutants at the regulatory or catalytic site. A PKR dominant negative mutant, [$Arg^{296}$]PKR, which contains a single amino acid substitution of arginine for the invariant lysine in the catalytic domain II at position 296 has been described (Visvanathan, K. V. & Goodbourne, S. (1989) *EMBO J.* 8, 1129–1138; D'Addario, M., Roulston, A., Wainberg, M. A. & Hiscott, J. (1990) *J. Virol.* 64, 6080–6089). This mutant protein [$Arg^{296}$]PKR can specifically suppress the activity of endogenous wild-type PKR in vivo. Additional mutants have been generated by altering the dsRNA binding motifs. For example, Feng et al. (Proc Natl Acad Sci USA 1992 89:5447–5451) abolished dsRNA binding ability of PKR by deletional analysis to obtain mutants with deletions between amino acid residues 39–50 or 58–69. Similarly, other investigators have mutated amino acid residues in the N-terminal region to suppress dsRNA binding ability leading to loss of PKR enzymatic activities (Green SR, Mathews M B. Genes & Development 1992 6:2478–2490; McCormack S J, Ortega L G, Doohan J P, Samuels C E. Virology 1994 198:92–99). A recent article has further identified two amino acid residues that are absolutely required for dsRNA binding, namely glycine 57 and lysine 60 (McMillan N A J, Carpick B W, Hollis B, Toone W M, Zamanian-Daryoush, and Williams B R G. J. Biol. Chem. 1995 270:2601–2606). Mutants in these positions were shown to be unable to bind dsRNA in vitro and possessed no antiproliferative activity in vivo when expressed in murine macrophage cells.

The physiological significance of the loss of PKR activity in vivo has been examined in animals. Catalytically inactive PKR mutants (including [$Arg^{296}$]PKR) when transfected into NIH 3T3 (mouse fibroblast) cells caused suppression of endogenous PKR activity in the transfectants. When administered to nude mice, these transfected cells caused tumor formation suggesting a tumor suppressor activity for PKR (Koromilas, A. E., Roy, S., Barber, G. N., Katze, M. G. & Sonenberg, N. (1992) *Science* 257, 1685–1689; Meurs, E. F., Galabru, J., Barber, G. N., Katze, M. G. & Hovanessian, A. G. (1993) *Proc. Natl. Acad. Sci. USA* 90, 232–236). Meurs et al. (J. Virol. 1992 66:5805) produced stable transfectants of NIH 3T3 cells with either a wild type (wt) PKR gene or a dominant negative mutant under control of a CMV promoter and showed that only transfectants receiving the wt clone were partially resistant to infection with encephalomyocarditis virus (EMCV). Lee et al. (Virol. 1993 193:1037) constructed a recombinant vaccinia virus vector containing the PKR gene under control of an inducible promoter and showed that in HeLa cells infected with the recombinant virus and induced resulted in an inhibition of the vaccinia virus protein and an overall decrease in viral yield. Henry et al. (J. Biol. Regulators and Homeostatic Agents 1994 8:15) showed that reoviral mRNAs containing a PKR activator sequence are poorly expressed in comparison with other reoviral mRNAs but that addition of 2-aminopurine, a PKR inhibitor, or transfection with a dominant negative PKR mutant, specifically increased the expression of mRNA containing the activator sequence. Maran et al. (Science 1994 265:789) showed that HeLa cells that were selectively deleted for PKR mRNA by treatment with PKR antisense oligos linked to 2'-5' oligoA were unresponsive to activation of nuclear factor-κB by the dsRNA poly(I):poly(C).

Several strategies have been utilized in the effort to improve the yield of virus obtained from cell culture for vaccine production. Different cell types have been tested to obtain the best cell line for optimum growth of specific viruses. The diploid human embryonic lung cell lines, MRC-5 and WI-38, have been developed specifically for vaccine production (see Pearson Devel. Biol. Standard. 1992 76:13–17; MacDonald, C. Critical Reviews Biotech. 1990 10:155–178; Wood et al. Biologicals 1990 18:143–146). Other attempts to improve vaccine production from cell culture include use of a low protein serum replacement factor (Candal et al. Biologicals 1991 19:213–218), and treatment of the cell culture with proteolytic enzymes (U.S. Pat. No. RE 33,164).

SUMMARY OF THE INVENTION

It is an object of the present invention to provide a method for enhanced vaccine production in cell culture. It is another object of the invention to provide methods for the evaluation of antiviral compounds and for the identification and culture of viral pathogens.

These objects are generally accomplished by providing animal cell cultures in which the expression of the interferon genes is substantially decreased from the normal level of expression. This may be effected by manipulating the level of expression of factors that function in vivo to regulate the interferon level, including interferon transcriptional regulators (for example, IRF1), interferon receptors and interferon stimulated gene products (for example PKR and 2-5A synthetase).

These objects are particularly accomplished by providing various methods using animal cell cultures in which the level of interferon-mediated antiviral protein activity, particularly for double-stranded RNA dependent kinase (PKR) and 2'-5' Oligoadenylate synthetase (2-5A synthetase), is significantly decreased from the normal levels. Among the various methods provided are methods for vaccine production, methods for determining the antiviral activity of a compound, and methods for detecting a virus in a sample.

BRIEF DESCRIPTION OF THE DRAWINGS

FIG. 1A Functional PKR activity was determined using a poly(I):poly(C)-cellulose assay for PKR autophosphorylation. Cell extracts were prepared from the different U937 transfectant cell lines following incubation with (+) or without (−) recombinant human IFN-α2 (200 U/mL) as indicated, while L929 cells were similarly treated with mouse IFN-α/β. Lane 1, HeLa; lanes 2 and 3, U937-neo; lane 4, U937-AS1; lane 5, U937-AS3; lane 6, U937-M13; lane 7, U937-M22; lane 8, L929. Positions of the human (68 kDa) and mouse (65 kDa) PKR proteins, and the molecular size standards (80 and 50 kDa) are indicated. FIG. 1B Cell extracts were prepared as above after induction with IFN-α or -γ and PKR protein levels were determined by Western blot analysis.

DESCRIPTION OF SPECIFIC EMBODIMENTS

Figure 1A:
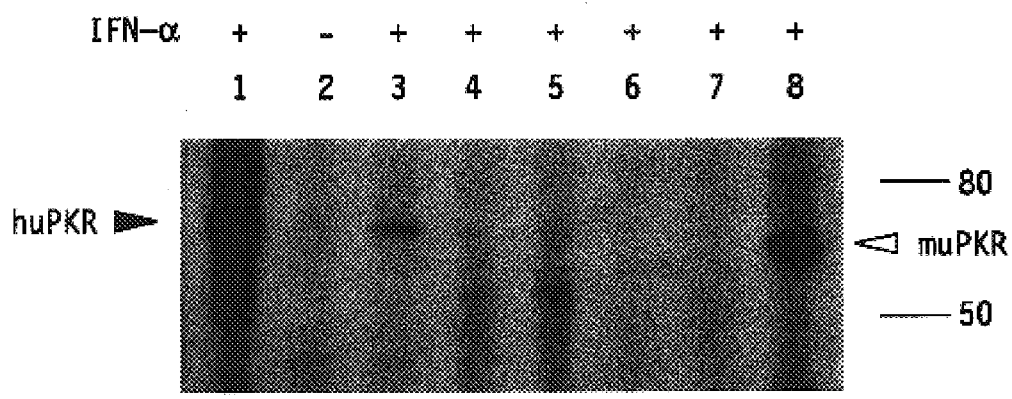
FIGS. 1A and 1B. PKR activity and protein levels in U937-derived stable transfectant cell lines.

The present invention relies upon the discovery by the inventor that the level of interferon production in cells can be regulated by manipulating the expression or activity of certain factors that normally regulate interferon expression and activity in vivo. These factors include certain interferon-specific transcriptional regulators, particularly IRF1, certain interferon receptors, as well as the gene products of certain interferon simulated genes (also called interferon-mediated antiviral responses), particularly PKR and 2-5A synthetase. Suppression or elimination of the expression or activity of any of these factors will result in a lower than normal level of expression of interferon genes. One consequence of this lower than normal interferon expression level is an increased permissiveness of the cell to viral replication. An increased permissiveness of the cell to viral reproduction means that greater viral production can be achieved in that cell relative to a cell having normal interferon expression. Cells having an increased permissiveness to viral replication are useful for a number of applications including vaccine production, sensitive detection of low levels of virus and for the evaluation of antiviral compounds.

The present inventor has surprisingly found that animal cells that are deficient in interferon-mediated antiviral responses, particularly cells deficient in dsRNA dependent kinase, 2N-5N Oligoadenylate synthetase or both, produce a higher viral yield when infected with an animal virus than cells with normal levels of these proteins. Increases of viral yield by as much as $10^3$ to $10^4$ or more can be obtained using the method of the present invention. The ability to obtain high yields of virus in PKR- or 2-5A synthetase-deficient cell culture makes it possible to produce large amounts of virus within a short time. This is particularly important for production of viral vaccines, most particularly for RNA virus, including influenza virus. The increased permissiveness of the deficient cells to viral replication makes them useful in a method for evaluating antiviral drugs in cell culture and in a method for detecting viral pathogens.

One aspect of the present invention provides a method for production of a viral vaccine in cell culture which comprises (a) infecting a cell culture with a donor strain animal virus, wherein said cell culture is deficient in the activity of the gene product of an interferon-stimulated gene, (b) culturing the infected cell culture under conditions sufficient to provide efficient virus growth, and (c) harvesting the virus produced. The harvested virus may be additionally prepared for vaccine use by purification, for instance by sterile filtration, ultrafiltration and/or concentration by column chromatography or other methods. The harvested virus may optionally be treated to inactivate the virus for the production of killed viral vaccines.

In a preferred embodiment, the cell culture is deficient in PKR activity. By PKR-deficient is meant that the PKR activity is less than 5% of the normal level of PKR activity. By normal level of PKR activity is meant the PKR activity observed in the parental cell culture from which the stable PKR-deficient cells are obtained or, if the PKR-deficiency is transiently induced, the PKR activity level observed in the cells before induction to PKR-deficiency. Preferably, the PKR-deficient cells have less than 1% of the normal level of PKR activity, more preferably the PKR-deficient cells have less than 0.1% of the normal level of PKR activity. By PKR activity is meant the ability to mediate the antiviral and antiproliferative activities of IFN-α and IFN-β, the ability to phosphorylate initiation factor e1F-2α, or the ability to phosphorylate IκBα to release nuclear factor κB. By PKR is meant human p68 kinase or any analog or homolog of human p68 kinase. By analog of human p68 kinase is meant any double-stranded RNA-dependent kinase that mediates ds-RNA activation of interferon transcription. Typically, such ds-RNA dependent kinases are p68 kinase equivalents present in other species, such as, for example, rabbits or mice and in different tissues among the various species. For example, murine p65 kinase is an analog of human p68 kinase. Another example of an analog of p68 kinase has been described in human peripheral blood mononuclear cells (Farrel et al.) By homolog is meant a protein homologous to at least one domain of human p68 kinase, such as, for example, the dsRNA-binding domain or the kinase domain. One such functional kinase homolog is yeast GCN2 kinase.

PKR-deficient cells can be obtained by any of a variety of methods that are well-known in the art. PKR-deficient mutants can be stably PKR-deficient or may be transiently induced to PKR-deficiency. Techniques for producing stable PKR-deficient mutants include, but are not limited to, random or site-directed mutagenesis (for example, Deng W P, and Nickoloff J A Analytical Biochemistry 1992 200:81–88; Busby S, Irani M, Crombrugghe B. J. Mol Biol 1982 154:197–209), targeted gene deletion ("gene knock-out") (for example, Camper S A, et al. Biology of Reproduction 1995 52:246–257; Aguzzi A, Brandner S, Sure U et al. Brain Pathology 1994 4:3–20), transfection with PKR antisense polynucleotides (for example, Lee et al. Virology 1993 192:380–385) and transfection with a PKR dominant negative mutant gene.

A PKR dominant mutant is a PKR mutant for which only a single allele need be expressed in order to suppress normal PKR activity. PKR dominant mutant genes include a mutant human p68 kinase, a mutant murine p65 kinase, and mutants of any other ds-RNA dependent kinases or mutants of analogs or homologs of human p68 kinase that suppress normal PKR activity, for example [Arg$^{296}$]PKR (Meurs et al. J. Virol. 1992 66:5805–5814). Examples of other PKR dominant mutants include mutants of PKR obtained from rabbit reticulocytes, different mouse tissues and human peripheral blood mononuclear cells (Farrel et al., Levin et al., Hovanessian, Krust et al., Buffet-Janvresse et al.) PKR dominant mutants include mutants of functional homologs that suppress protein synthesis by interfering with initiation factor phosphorylation, particularly phosphorylation of eIF-2α. One such functional kinase homolog mutant is a mutant of yeast GCN2 kinase.

Techniques for producing cells that are transiently PKR-deficient include, but are not limited to, use of 2'-5' oligoadenylate-linked PKR antisense oligonucleotides (Maran, A., Maitra, R. K., Kumar, A., Dong, B., Xiao, W., Li, G., Williams, B. R. G., Torrence, P. F. & Silverman, R. H. (1994) *Science* 265, 789–792) or specific inhibitors of the PKR protein, such as 2-aminopurine (Marcus, P. I. & Sekellick, M. J. (1988) *J. Gen. Virol.* 69, 1637–45, Zinn, K., Keller, A., Whittemore, L. A. & Maniatis, T. (1988) *Science* 240, 210–3) as well as other competitive inhibitors that can block phosphorylation of PKR substrates, or inhibitors that can block double-stranded RNA binding. Transiently PKR-deficient cell cultures can be obtained by culturing a cell line in the presence of such antisense oligonucleotides or inhibitors.

Preferably for use in the method of the present invention, cell cultures will be stably PKR-deficient. Typically, PKR-deficient cell cultures are produced by transfection of a parent cell line, preferably a cell line currently used in vaccine production, preferably MRC-5, WI-38, or Vero (African Green Monkey cell), with a vector containing a functional PKR antisense gene construct or a PKR dominant negative mutant construct followed by selection of those cells that have received the vector. A functional PKR antisense gene construct may be prepared by conventional methods; for example, by cloning a PKR cDNA such as that described in Meurs et al. (Cell 1990 62:379–390), in an antisense orientation, under the control of an appropriate promoter, for example a CMV promoter. A PKR dominant negative mutant construct can be prepared by cloning the cDNA for a PKR dominant negative mutant, for example the cDNA for [Arg$^{296}$]PKR, under the control of an appropriate promoter.

Preferably the PKR mutant gene constructs are cloned under the control of an inducible promoter to reduce the risk of tumor formation by these PKR-deficient cells since the cells are to be used for vaccine production in the methods of the invention. This method will ensure the safety of the vaccines produced by these cells. The loss of PKR activity has been associated with tumor formation (Koromilas et al.; Meurs et al.). Although the harvested virus can be purified from cell culture components, there nevertheless remains a risk that some PKR-deficient cells would be carried over into the final vaccine preparation. If PKR activity remains constitutively suppressed, these cells may potentially become tumorigenic. This would create potential health risk for the vaccine recipient. However, if an inducible promoter is used to control expression of the gene construct, endogenous PKR activity would be restored upon removal of the inducer. Suitable inducible promoters include a lac promoter, a heat shock promoter, a metallothionein promoter, a glucocorticoid promoter, or any other inducible promoter known to one skilled in the art.

Other ways of constructing similar vectors, for example using chemically or enzymatically synthesized DNA, fragments of the PKR cDNA or PKR gene, will be readily apparent to those skilled in the art. Transfection of the parental cell culture is carried out by standard methods, for example, the DEAE-dextran method (McCutchen and Pagano, 1968, J. Natl. Cancer Inst. 41:351–357), the calcium phosphate procedure (Graham et al., 1973, J. Virol. 33:739–748) or by any other method known in the art, including but not limited to microinjection, lipofection, and electroporation. Such methods are generally described in Sambrook et al., Molecular Cloning: A laboratory manual, 2nd Edition, 1989, Cold Spring Harbor Laboratory Press. Transfectants having deficient PKR activity are selected. For ease of selection, a marker gene such as neomycin phosphotransferase II, ampicillin resistance or G418 resistance, may be included in the vector carrying the antisense or mutant gene. When a marker gene is included, the transfectant may be selected for expression of the marker gene (e.g. antibiotic resistance), cultured and then assayed for PKR activity.

Residual PKR activity in PKR-deficient cells can be determined by any of a number of techniques that are well-known in the art. The activity of PKR can be determined directly by, for example, an autophosphorylation assay such as that described in Maran et al. (Science 265:789–792 1994) or Silverman et al. (Silverman, R. H., and Krause, D. (1986) in *Interferons: A practical approach*. Morris, A. G. and Clemens, M. J., eds. pp. 71–74 IRL Press, Oxford-Washington, D.C.). Typically, an autophosphorylation assay for PKR activity is carried out as follows. Extracts from cells to be examined for PKR activity which contain approximately 100 μg of protein are incubated with 20 μl of poly(I):poly(C)-cellulose beads for 60 min on ice. The kinase is immobilized and activated on the beads. After washings of the polynucleotide cellulose-bound kinase fractions, an autophosphorylation reaction is performed at 30° C. for 30 min in an assay solution. The assay solution contains 1 μCi of [γ$^{32}$P]ATP, 1.5 mM magnesium acetate, 10 μM ATP pH 7.5, 0.5% NP 40, and 100 μg/ml leupeptin. The samples are heated at 90° C. for 3 min in gel sample buffer containing sodium dodecyl sulfate (SDS) and the proteins are analyzed by 10% SDS-polyacrylamide gel electrophoresis. The gels are dried and autoradiographs are prepared using XAR-5 X-ray film (KodaK).

Residual PKR activity may also be determined indirectly by assaying for the presence of the PKR protein, for example by Western blot with PKR specific antibodies, or for the presence of PKR RNA, for example by Northern blot with oligonucleotide or cDNA probes specific for PKR. As will be readily apparent, the type of assay appropriate for determination of residual PKR activity will in most cases depend on the method used to obtain the PKR-deficient phenotype. If, for example, the method used to produce the PKR-deficient cell results in suppression or elimination of PKR gene expression (for example, gene knock-out), analysis techniques that detect the presence of mRNA or cDNA (e.g. Northern or Southern blots) or the presence of the protein (e.g. Western blot) or that detect the protein activity may be useful to determine the residual PKR activity in the PKR-deficient cells. On the other hand, if the method used to produce the PKR-deficient cells results in inhibition of the protein rather than elimination of expression of the gene (for instance, transfection with a vector carrying a dominant negative PKR mutant), an autophosphorylation assay is more appropriate than a Western blot for determination of the residual PKR activity.

In another embodiment, the present invention provides a method for production of a viral vaccine in a cell culture that is deficient in 2'-5' Oligoadenylate synthetase activity. A cell culture deficient in 2-5A synthetase can be isolated in a similar fashion to cell cultures deficient in PKR, for example, random or site-directed mutagenesis, targeted gene deletion of the 2-5A synthetase genes or transfection with antisense 2-5A synthetase constructs. By 2-5A synthetase-deficient is meant that the 2-5A synthetase activity is less than 5% of the normal level of 2-5A synthetase activity. By normal level of 2-5A synthetase activity is meant the 2-5A synthetase activity observed in the parental cell culture from which the stable 2-5A synthetase-deficient cells are obtained or, if the 2-5A synthetase-deficiency is transiently induced, the 2-5A synthetase activity level observed in the cells before induction to 2-5A synthetase-deficiency. Preferably, the 2-5A synthetase-deficient cells have less than 1% of the normal level of 2-5A synthetase activity, more preferably the 2-5A synthetase-deficient cells have less than 0.1% of the normal level of 2-5A synthetase activity. Residual 2-5A synthetase activity in 2-5A synthetase-deficient cells can be determined by methods similar to those used for determining residual PKR activity, that is, Western blots using 2-5A synthetase specific antibodies, Northern blots using oligonucleotide or cDNA probes specific for 2-5A synthetase or enzyme activity assays (see, Read et al. J. Infect. Dis. 1985 152:466–472; Hassel and Ts'o J. Virol. Methods 1994 50:323–334). Typically, 2-5A synthetase activity is determined as follows. Cells to be assayed are treated with IFN-$\alpha_2$ (100 U/1 ml in RPMI plus 10% fetal bovine serum). Briefly, the cell cultures are incubated for 18 hr at 37° C., washed and the cell pellets are treated with cell lysis buffer for 10 min at 4° C. Aliquots of the cellular extract are incubated with poly(I):poly(C)agarose beads for 30 min at 30° C., to allow for binding as well as activation of the 2-5A synthetase enzyme. The beads are washed and then incubated in an assay solution containing 3 mM ATP, 4 $\mu$Ci$^3$H-ATP per assay sample, and 20 mM Hepes buffer pH 7.5 for 20 hr at 30° C. Following incubation, the samples are heated at 90° C. to inactivate the enzyme, followed by treatment with bacterial alkaline phosphatase (BAP). The 2-5 oligoA synthesized is resistant to BAP. The amount of 2-5 oligo A is determined by spotting a sample onto filter paper, washing and counting the H radioactivity using a scintillation counter. The amount of oligoA product produced is correlated with the enzyme activity by conventional methods. Alternatively, 2-5A synthetase can be assayed by a radioimmune and radiobinding method (Knight M, et al. Radioimmune, radiobinding and HPLC analysis of 2-5A and related oligonucleotides from intact cells Nature 1980 288:189–192).

It will be apparent that cell cultures deficient in both PKR activity and 2-5A synthetase activity can be made by a combination of the methods described above. The doubly deficient cell cultures can be prepared either sequentially (that is, by first selecting cultures deficient in one activity and then using that cell culture as the starting material for preparing the second deficient culture) or simultaneously (selection for both deficiencies at once).

In another embodiment, the present invention provides a method for production of a viral vaccine in a cell culture that is deficient in human MxA protein activity. A cell culture deficient in human MxA protein activity can be isolated in a similar fashion to cell cultures deficient in PKR, for example, random or site-directed mutagenesis, targeted gene deletion of the MxA genes or transfection with antisense MxA constructs. By MxA protein-deficient is meant that the MxA activity is less than 5% of the normal level of MxA activity. By normal level of MxA activity is meant the MxA activity observed in the parental cell culture from which the stable MxA-deficient cells are obtained or, if the MxA-deficiency is transiently induced, the MxA activity level observed in the cells before induction to MxA-deficiency. Preferably, the MxA-deficient cells have less than 1% of the normal level of MxA activity, more preferably the MxA-deficient cells have less than 0.1% of the normal level of MxA activity. Residual MxA activity in MxA-deficient cells can be determined by methods similar to those used for determining residual PKR activity, that is, Western blots using MxA specific antibodies, Northern blots using oligonucleotide or cDNA probes specific for MxA or enzyme activity assays (Garber et al. (1991) *Virology* 180, 754–762; Zurcher et al. (1992) *Journal of Virology* 66, 5059–5066). Typically, MxA activity is determined as described in Zurcher et al.

In yet another embodiment, the present invention provides a method for production of a viral vaccine in a cell culture that is deficient in interferon responsiveness. By interferon responsiveness is meant the ability of a cell to respond to stimulation by interferon. A cell culture deficient in interferon responsiveness can be obtained by culturing the cells in the presence of an inhibitor of an interferon receptor. Alternatively, cells can be engineered to express, in the absence of a normal interferon receptor, a mutant interferon receptor that is unresponsive to interferon.

In another embodiment, the present invention provides a method for production of a viral vaccine in a cell culture that is deficient in interferon-specific transcriptional regulators. One such interferon-specific transcriptional regulator is IRF1. Cells stably deficient in interferon-specific transcriptional regulators can be obtained by any of a number of techniques well known in the art, such as, for example, random or site-directed mutagenesis, targeted gene deletion, or transfection with antisense vectors. Transiently deficient cells can be obtained by culturing cells in the presence of antisense oligonucleotides or specific inhibitors of interferon transcription.

The method of the present invention can be practiced with a variety of animal cell cultures, including primary cell cultures, diploid cell cultures and continuous cell cultures. Particularly useful are cell cultures that are currently used for the production of vaccine, most particularly those cell cultures that have been approved for vaccine production by the USFDA and or WHO, for example, MRC-5, a human diploid cell line from fetal lung tissue (Nature Lond. 1970 227:168–170) and WI-38, a human diploid cell line derived from embryonic lung tissue (Am. J. Hyg. 1962 75:240; First International Conference on Vaccines Against Viral and Rickettsial Diseases of Man, Pan American Health Organization, Pub. No. 147: 581 May 1981). Also useful are Chang liver cells (Chang, R S Proc. Soc. Exp. Biol. Med. 1954 87:440), U937 human promonocytic cells (Sundstrom et al. Int. J. Cancer 1976 17:565–577), Vero cells, MRC-9 cells, 1MR-90 cells, 1MR-91 cells and Lederle 130 cells (Biologicals 18:143–146 1991). U937 cells are particularly useful for viruses that infect immune cells expressing CD4, for example, HIV. For a general review of cell cultures used in the production of vaccines see Grachev, V. P. in *Viral Vaccines* Mizrahi, A. ed. pages 37–67 1990 Wiley-Liss. The particular cell culture chosen will depend on the virus which is to be produced; in general, the cell culture will be derived from the species which is the natural host for the virus, although this is not essential for the practice of the present invention (for example, human virus can be grown on a canine kidney cell line (MDCK cells) or a green monkey kidney cell line (Vero cells; Swanson et al. J. Biol. Stand. 1988 16:311)). Typically, the cells chosen will be PKR-deficient or 2-5A synthetase-deficient derivatives of cells or cell lines known to be an appropriate host for the virus to be produced. For example, for influenza virus and hepatitis A virus vaccines, preferred host cells are derivatives of MRC-5. For HIV vaccine production, preferred host cells are derivatives of U937, H9, CEM or CD4-expressing HUT78 cells. Cell lines used for the production of vaccines are well known and readily available from commercial suppliers, for example, American Type Culture Collection.

The infection of the interferon-mediated antiviral response-deficient cells with donor virus according to the present invention is carried out by conventional techniques (see for example Peetermans, J. Vaccine 1992 10 supp 1:S99–101; Shevitz et al. in *Viral Vaccines* Mizrahi, a. ed. pp 1–35 1990 Wiley-Liss). Typically, virus is added to the cell culture at between 0.001 to 0.5 $TCID_{50}$ per cell, preferably at 0.01 to 0.10 $TCID_{50}$ per cell, but will vary as appropriate for the particular virus and cell host being used. As is readily apparent to one of ordinary skill in the art, every cell of the cell culture need not be infected initially for efficient viral production. The infected cells are cultured under conditions appropriate for the particular cells and viral production at various times after infection is monitored. Viral production can be monitored by any of a number of standard techniques including plaque-forming unit assays, $TCID_{50}$ assays or hemagglutination inhibition assays (Robertson et al. J. Gen. Virol. 1991 72:2671–2677). The infected cells are cultured under conditions sufficient to provide efficient viral growth. The cells can be cultured until maximum viral production is achieved as indicated by a plateauing of the viral yield. The virus is harvested by standard techniques and substantially purified from other cellular components (see for example, Peetermans 1992). The harvested virus may be used as a live viral vaccine, either fully virulent or attenuated, or may be inactivated before use by methods that are well-known in the art, for example, by treatment with formaldehyde (Peetermans, J Vaccine 1992 10 Suppl 1:S99–101; U.S. Pat. No. RE 33,164).

The vaccine may be available in dry form, to be mixed with a diluent, or may be in liquid form, preferably in aqueous solution, either concentrated or ready to use. The vaccine is administered alone or in combination with pharmaceutically acceptable carriers, adjuvants, preservatives, diluents and other additives useful to enhance immunogenicity or aid in administration or storage as are well-known in the art. Suitable adjuvants include aluminum hydroxide, alum, aluminum phosphate, Freunds or those described in U.S. Pat. Nos. 3,790,665 and 3,919,411. Other suitable additives include sucrose, dextrose, lactose, and other non-toxic substances. The vaccines are administered to animals by various routes, including intramuscular, intravenous, subcutaneous, intratracheal, intranasal, or by aerosol spray and the vaccines are contemplated for the beneficial use in a variety of animals including human, equine, avian, feline, canine and bovine.

The method of the present invention can be practiced with a variety of donor animal viruses. By donor virus is meant the particular viral strain that is replicated in vitro to produce the vaccine. The particular donor animal virus used will depend upon the viral vaccine desired. Donor viruses currently used for vaccine production are well-known in the art and the method of the present invention can be readily adapted to any newly identified donor virus. Preferred donor viruses include human influenza virus, especially influenza A (H3N2) and influenza A (H1N1) (see U.S. Pat. No. 4,552,758; ATCC Nos. VR-2072, VR-2073, VR-897); influenza A described in U.S. Pat. No. 3,953,592; influenza B (U.S. Pat. No. 3,962,423; ATCC Nos. VR-786, VR-791); and Parainfluenza 1 (Sendai virus) (Cantell et al. Meth. Enzymol. 78A:299–301 1980; ATCC No.VR-907). The donor virus can be identical to the viral pathogen or may be a naturally-occurring attenuated form, an attenuated form produced by serial passage through cell culture or a recombinant or reassortant form. Any viral strain may be used as donor virus provided that it retains the requisite antigenicity to afford protection against the viral pathogen. The method of the present invention is particularly useful with attenuated or poorly replicating donor viruses.

Some of the vaccines that can be provided by the methods of the present invention include, but are not limited to, human vaccines for poliovirus, measles, mumps, rubella, hepatitis A, influenza, parainfluenza, Japanese encephalitis, cytomegalovirus, HIV, Dengue fever virus, rabies and Varicella-zoster virus, as well as many non-human animal vaccines including, for example, vaccines for feline leukemia virus, bovine rhinotracheitis virus (red nose virus), cowpox virus, canine hepatitis virus, canine distemper virus, equine rhinovirus, equine influenza virus, equine pneumonia virus, equine infectious anemia virus, equine encephalitis virus, ovine encephalitis virus, ovine blue tongue virus, rabies virus, swine influenza virus and simian immunodeficiency virus. As will be apparent from the foregoing, the method of the present invention is not limited to vaccine production for human viruses but is equally suitable for production of non-human animal viral vaccines.

Another aspect of the present invention provides a method for evaluating the activity of antiviral compounds. Due to the increased permissiveness of the PKR-deficient cells to viral replication, the cells are useful in a sensitive assay for assessing the effectiveness of antiviral compounds. In this aspect, the present invention comprises the steps of (a) treating a virus, virus-infected host cells or host cells prior to virus infection with the antiviral compound and (b) assaying for the presence of remaining infectious virus by exposure under infective conditions of a PKR-deficient or 2-5A synthetase-deficient indicator cell culture.

In this aspect, the virus against which the antiviral compound is to be tested may be treated directly with the compound. In this case, the treated virus may then be analyzed directly for the presence of remaining infectious virus by exposure under infective conditions of a PKR-deficient or 2-5A synthetase-deficient indicator cell culture to an aliquot of the treated virus, culturing for a time sufficient to allow replication of any remaining infectious virus and analyzing the indicator culture for the presence of the replicated virus. Alternatively, the virus against which the antiviral compound is to be tested may be used to infect a host cell culture, the infected host cell culture is then treated with the antiviral compound. A cell extract of the treated infected host cell culture is prepared by conventional techniques and an aliquot of the extract is analyzed for the presence of remaining infectious virus by exposure to a PKR-deficient or 2-5A synthetase-deficient indicator cell culture as described above. In another alternative, the host cell culture may be treated with the antiviral compound prior to infection with the virus rather than after infection. The treated cells are then infected with the virus against which the antiviral compound is to be tested, cultured and analyzed for the presence of replicated virus. The particular treatment regime chosen will depend upon the known or postulated mode of action of the antiviral compound and will be readily within the determination of one skilled in the art. By exposure under infective conditions is intended the bringing together the deficient indicator cell culture and an aliquot of the treated sample (either virus or infected cell extract) under conditions that would result in infection of the deficient cell culture if any virus was present in the treated sample. After exposure to the treated sample, the deficient indicator cell culture is cultured further and assayed for the replication of the virus, by standard method (for example, plaque assays or $TCID_{50}$ assays or Northern or Western analysis for viral RNA or protein).

The host cell culture may be any cell culture which is susceptible to infection by the virus against which the antiviral compound is to be tested. The indicator cell culture is a PKR-deficient or 2-5A synthetase deficient cell culture that is used to assay for infectious virus remaining after treatment with the antiviral compound. The indicator PKR-deficient or 2-5 A synthetase deficient cell culture is prepared as described above for vaccine production. Cells suitable as a parent for generating the deficient indicator are the same as those that are useful for generating the PKR-deficient or 2-5A synthetase deficient cell cultures for vaccine production. In addition, the following cell lines are also suitable: hepatoma cell lines in general, particularly Hep G2 human hepatocellular carcinoma (Nature 1979 282:615–616; U.S. Pat. No. 4,393,133) and Hep 3B (U.S. Pat. No. 4,393,133). It will be apparent that the indicator cell culture is also susceptible to infection by the virus against which the antiviral compound is to be treated. The host cell culture and the indicator cell culture may be the same or different. The antiviral compound can be any chemical or biological preparation suspected of having some antiviral activity. If the virus itself is treated with the antiviral compound, the compound may be removed before infection of the indicator cell culture by exposure to the treated virus. If an infected host cell culture (or a pre-infected host cell culture) is treated with the antiviral compound, the compound may be removed before preparation of the cell extract.

In a separate related aspect, the present invention provides a method for identification and culture of viral pathogens. The permissiveness of PKR-deficient cells to viral replication makes them particularly useful in a method to detect very low levels of virus and/or viruses that are difficult to culture, for example, HIV in monocytes or lymphocytes of neonates. In this aspect the present invention comprises the steps of (1) exposing under infective conditions a PKR-deficient or a 2-5A synthetase-deficient cell culture to a sample suspected of containing a virus and (2) assaying for the presence of replicated virus in the exposed cells. The practice of this aspect of the present invention is similar to that of the previous aspect except that treatment with antiviral compound is omitted. In this aspect, the sample to be assayed for the presence of virus is generally a clinical sample from a patient suspected of having a viral infection. The sample may be any appropriate clinical sample including blood, saliva, urine, as well as biopsy samples from lymph node, lung, intestine, liver, kidney and brain tissue. The sample may be treated appropriately to release viral particles (for example, cell extracts may be prepared) or the sample may be used as received from the patient. The sample or an aliquot of the sample is exposed under infective conditions to a deficient indicator cell culture and the presence of any replicating virus is determined as described above.

Specific examples of the steps described above are set forth in the following examples. However, it will be apparent to one of ordinary skill in the art that many modifications are possible and that the examples are provided for purposes of illustration only and are not limiting of the invention unless so specified.

EXAMPLES

Example 1

Preparation of Plasmids

The cDNA inserts corresponding to the wild type human PKR gene and the dominant negative [$Arg^{296}$]PKR mutant gene, from the plasmids pBS-8.6R and yex6M (Meurs E, Chong K, Galabru J. et al. Cell 1990 62: 379–90; Chong et al. EMBO J. 11:1553–1562 1992), respectively, were released by HindIII digestion and subcloned into pRC-CMV (Invitrogen), a constitutive eukaryotic expression plasmid containing a G418-resistance marker. The orientation of the inserts in selected clones was determined by restriction digest analysis and confirmed by sequencing (Sequenase 2.0, USB). This procedure resulted in the isolation of the expression plasmids used, pPKR-AS (containing the PKR cDNA in an antisense orientation under the control of the CMV promoter in the vector) and p[$Arg^{296}$]PKR (containing the $Arg^{296}$PKR cDNA under the control of the CMV promoter in the vector).

Example 2

Isolation of PKR-Deficient Stable Transfectants

Stable transfectants were obtained by electroporation of $5\times10^6$ exponentially growing U937 cells with 10 μg of each plasmid, in serum-free RPMI-1640 containing DEAE-dextran (50 μg/mL), with a Gene Pulser apparatus (BioRad) set at 500 μF, 250V. Bulk populations of stable transfectants were obtained by selection with 400 μg/mL geneticin (GIBCO-BRL) for 3 weeks. Clonal lines were subsequently obtained by limiting dilution cloning. Cell lines were cultured in RPMI-1640 containing 10% fetal calf serum (complete media) and geneticin.

Five representative cell lines were selected for initial characterization: "U937-neo" (also called U9K-C) was the control cell line transfected with the parental vector, pRC-CMV; "U937-AS1" (also called U9K-A1) and "U937-AS3" (also called U9K-A3) were independent clones transfected with pPKR-AS; "U937-M13" (also called U9K-M13) and "U937-M22" (also called U9K-M22) were independent clones transfected with p[$Arg^{296}$]PKR.

Example 3

Characterization of PKR-Deficient Transfectants

PKR kinase activity was measured in an autophosphorylation assay that uses poly(I):poly(C)-cellulose for binding and activation of PKR enzyme. PKR autophosphorylation assay was performed essentially as described by Maran et al. with the following modifications. Cell extracts (100 μg of protein per assay) were incubated with poly(I):poly(C)-cellulose for 1 hour on ice, washed three times, and incubated for 30 minutes at 30° C. in 50 μl of a reaction buffer (20 mM HEPES (pH 7.5), 50 mM KCl, 5 mM 2-mercaptoethanol, 1.5 mM Magnesium acetate, 1.5 mM $MnCl_2$) containing 1 μCi of [$\gamma$-$^{32}$P]ATP. Proteins were separated on a 10% SDS-polyacrylamide gel and analyzed by autoradiography.

Cell extracts from IFN-treated HeLa and mouse L929 cells were used as positive controls, since PKR activity in these cells has been previously characterized (Meurs et al.) (FIG. 1A, lanes 1 and 8). U937-neo cells contained low basal levels of PKR activity which increased following treatment with IFN-α: (FIG. 1A, lanes 2 and 3). PKR activity in the parental, untransfected U937 cells was similar to U937-neo cells. However, PKR activity was not detected in any of the four cell lines transfected with pPKR-AS or p[Arg$^{296}$]PKR plasmids. Furthermore, treatment of these cells with IFN-α did not restore PKR activity (FIG. 1A, lanes 4–7), nor did treatment with IFN-γ.

Example 4

Western Analysis of PKR-Deficient Transfectants

To further confirm the inhibition of PKR expression in the pPKR-AS-transfected cell lines, Western blot analysis was performed using a monoclonal antibody specific for human PKR. Cell extracts (100 μg) were separated on a 10% SDS-polyacrylamide gel and electrotransferred onto nitrocellulose membrane. The membranes were incubated with anti-PKR monoclonal antibody (Meurs et al. Cell 1990) at 1:1000 in BLOTTO (5% nonfat dry milk, 0.05% Tween-20 in Tris-buffered saline). Final detection of PKR was facilitated by probing with a secondary horseradish peroxidase-conjugated goat anti-mouse antibody (Santa Cruz Biotech) and using a chemiluminesence method (Amersham ECL).

Figure 1B:
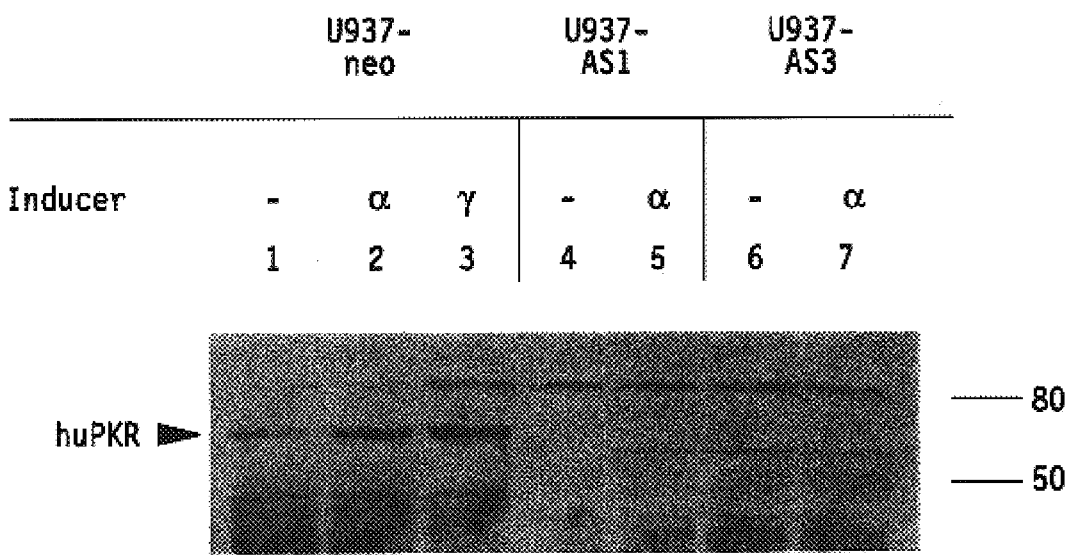
Figure 2A:
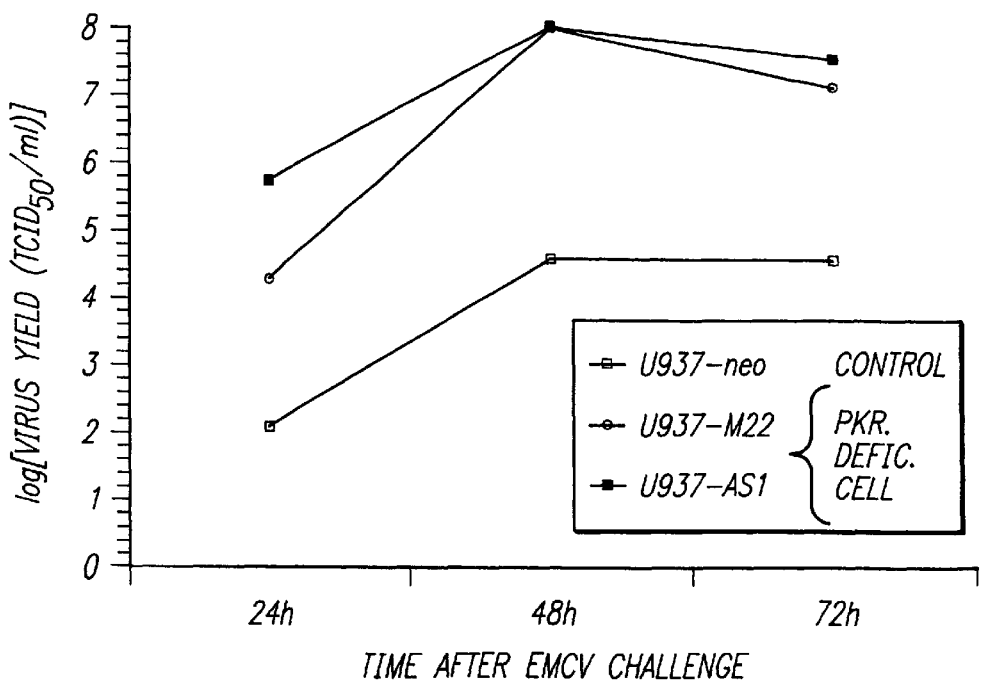
FIGS. 2A and 2B. Kinetics of EMCV replication are enhanced in PKR-deficient cells. The different U937 cell lines were challenged with EMCV at 0.1 (FIG. 2A) or 0.001 (FIG. 2B) $TCID_{50}$/cell. Samples were harvested at the indicated times and viral yields were measured in terms of $TCID_{50}$.
Figure 2B:
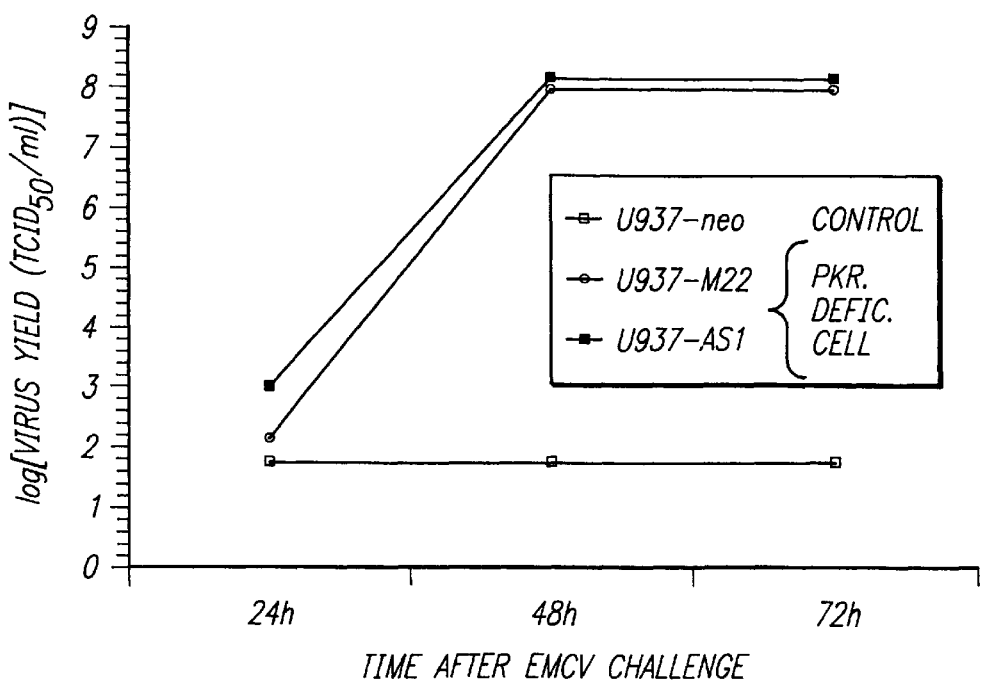

Basal level of PKR protein was detectable in U937-neo cells (FIG. 1B, lane 1) and increased following treatment with IFN-α or IFN-γ (FIG. 1B, lanes 2 and 3). In contrast, PKR expression was significantly diminished in both U937-AS1 and U937-AS3 cells (FIG. 1B, lanes 4 and 6) and did not increase following treatment with IFN-α (FIG. 1B, lanes 5 and 7). While PKR protein was detectable in U937-M13 and U937-M22 cells, the mutant [Arg$^{296}$]PKR protein was not distinguishable from wild type PKR by using Western blot analysis.

Example 5

Enhanced EMCV Replication in PKR-Deficient Cells

Since the IFN system plays a major role in antiviral responses, we investigated whether loss of PKR function would affect the rate of encephalomyocarditis virus (EMCV) replication. Stocks of EMCV (ATCC No. VR-1314) were prepared by passage in L929 cells. For determination of EMCV replication, U937-derived transfectants were cultured in complete media with or without IFNs (recombinant human IFN-α2, Schering; recombinant human IFN-γ, Amgen) for 18 hours. Following two washings with PBS, the cells were incubated with EMCV in serum-free media for 2 hours. The cells were washed again twice and replenished with media containing 1% FCS. Samples were collected at the required time points and lysed by three rounds of freeze-thaw. Four-fold serial dilutions of the samples were added onto L929 monolayers and incubated for 48 hours, followed by staining with 0.05% crystal violet to determine cytopathic effects and median tissue culture infective dose ($TCID_{50}$).

In the control U937-neo cell line following challenge with EMCV at 0.1 $TCID_{50}$/cell, viral titers peaked at approximately $10^4$ $TCID_{50}$/mL after 48 hours and did not increase further after 72 hours (FIG. 2A). However, in U937-AS1 and U937-M22 cells, EMCV replication was substantially higher reaching titers of $10^4$ to $10^5$ $TCID_{50}$/mL after only 24 hours and $10^8$ $TCID_{50}$/mL by 48 hours, representing a $10^3$ to $10^4$ increase in viral yield over that obtained in control cells. In separate experiments using a lower virus inoculum of 0.001 $TCID_{50}$/cell, more dramatic differences were observed in EMCV susceptibility between the control and the PKR-deficient cells (FIG. 2B). Under these conditions, EMCV replication in U937-neo cells was minimal, not exceeding $10^2$ $TCID_{50}$/mL even after 72 hours, while high viral titers of $10^8$ $TCID_{50}$/mL were attained after 48 hours in both U937-AS1 and U937-M22 cells. The results indicated that by suppressing PKR activity in vivo, the cells become very permissive to viral replication, showing as much as a thousand-fold increase over control cells.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the described invention.

What is claimed is:

1. A method for the production of a viral vaccine for human use, comprising:

(a) selecting a cell for the production of a viral vaccine, said cell having a targeted deletion in at least one gene selected from the group consisting of a protein kinase RNA-dependent (PKR) gene, a 2'-5'-linked oligoadenylate (2-5A) synthetase gene, and an Mx gene, wherein said cell has increased permissiveness to viral replication due to decreased expression or activity of interferon as a result of said targeted deletion;

(b) exposing said cell under infective conditions to a virus or a sample suspected of containing a virus, (c) culturing said exposed cell under conditions sufficient to provide efficient viral replication, (d) harvesting the virus produced, and (e) preparing said viral vaccine from said harvested virus.

2. The method of claim 1, further comprising inactivating the virus produced thereby for the production of a viral vaccine.

3. The method of claim 1, wherein said cell is deficient in interferon-mediated antiviral responses relative to the cell without the targeted deletion.

4. The method of claim 1, further comprising determining viral titer prior to said harvesting step.

5. The method of claim 1, wherein the viral vaccine is suitable for human administration.

6. The method of claim 1, further comprising packaging the virus produced thereby alone or with a pharmaceutically acceptable carrier.

7. A method for the production of a viral vaccine for human use, comprising:

(a) selecting a cell used for the production of a vaccine, said cell having a targeted deletion in a protein kinase RNA-dependent (PKR) gene, wherein the cell has increased permissiveness of the cell to viral replication due to a decreased interferon-mediated antiviral response as a result of said targeted deletion;

(b) exposing said cell under infective conditions to a virus or a sample suspected of containing a virus, (c) culturing said exposed cell under conditions sufficient to provide efficient viral replication, (d) harvesting the virus produced, and (e) preparing said viral vaccine from said harvested virus.

8. The method of claim 7, further comprising inactivating the virus produced thereby for the production of a viral vaccine.

9. The method of claim 7, herein the cell is further has a targeted deletion in a 2-5A synthetase gene.

10. The method of claim 7, wherein the cell is further has a targeted deletion in a Mx gene.

11. The method of claim 7, further comprising determining viral titer prior to said harvesting step.

12. The method of claim 7, wherein the viral vaccine is suitable for human administration.

13. The method of claim 7, further comprising packaging the virus produced thereby alone or with a pharmaceutically acceptable carrier.

* * * * *